(12) United States Patent
Unger et al.

(10) Patent No.: US 10,933,219 B2
(45) Date of Patent: Mar. 2, 2021

(54) TISSUE RETRACTION DEVICE AND DELIVERY SYSTEM

(71) Applicant: BOSTON SCIENTIFIC SCIMED, INC., Maple Grove, MN (US)

(72) Inventors: John Unger, Wrentham, MA (US); Christopher K. Oto, Boston, MA (US); Danny Shu-Huan Lee, Cambridge, MA (US); Ryan Wales, Northborough, MA (US); Alexander Joseph Burnham, Southbury, CT (US); Tracy Andreotti, Milford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 6 days.

(21) Appl. No.: 16/399,459

(22) Filed: Apr. 30, 2019

(65) Prior Publication Data

US 2019/0336728 A1    Nov. 7, 2019

Related U.S. Application Data

(60) Provisional application No. 62/665,441, filed on May 1, 2018.

(51) Int. Cl.
*A61B 17/02* (2006.01)
*A61B 17/3205* (2006.01)
(Continued)

(52) U.S. Cl.
CPC ..... *A61M 25/0082* (2013.01); *A61B 1/00087* (2013.01); *A61B 17/0218* (2013.01);
(Continued)

(58) Field of Classification Search
CPC .......... A61M 25/0026; A61M 25/0082; A61B 17/3205; A61B 17/0218; A61B 17/1285;
(Continued)

(56) References Cited

U.S. PATENT DOCUMENTS

| 3,958,576 A | 5/1976 | Komiya |
| 5,242,456 A | 9/1993 | Nash et al. |

(Continued)

FOREIGN PATENT DOCUMENTS

| CN | 203138577 U | 8/2013 |
| WO | 2008045940 A2 | 4/2008 |

OTHER PUBLICATIONS

Sakamoto, N., et al., "Endoscopic submucosal dissection of large colorectal tumors by using a novel spring-action S-O clip for traction (with video)", Gastrointestinal Endoscopy 69(7):1370-1374 (2009).

(Continued)

*Primary Examiner* — Pedro Philogene
(74) *Attorney, Agent, or Firm* — Kacvinsky Daisak Bluni PLLC

(57) ABSTRACT

Medical devices and methods of using medical devices are disclosed. An example tissue retraction device includes a first tissue engagement member coupled to an elastic member by a coupling assembly. The coupling assembly including a first coupler body having a first end region and a first compression member. Further, the first end region of the first coupler body is configured to extend into a portion of a lumen of the elastic member and the compression member is designed to compress the elastic member onto the first coupler body such that the elastic member is fixedly engaged with the coupler body.

20 Claims, 14 Drawing Sheets

(51) Int. Cl.
    *A61B 1/00*    (2006.01)
    *A61M 25/00*   (2006.01)
    *A61B 17/00*    (2006.01)
    *A61M 25/09*    (2006.01)

(52) U.S. Cl.
    CPC ..... *A61B 17/3205* (2013.01); *A61M 25/0026* (2013.01); *A61B 2017/0034* (2013.01); *A61B 2017/00269* (2013.01); *A61M 2025/09183* (2013.01)

(58) Field of Classification Search
    CPC ........ A61B 17/1227; A61B 2017/0034; A61B 2017/00477; A61B 2017/00862; A61B 2017/0225; A61B 2017/0287; A61B 2017/00269; A61B 2025/09183; A61B 1/00087; A61B 1/018
    USPC .......... 606/139–157, 205–211; 600/201–235
    See application file for complete search history.

(56)         References Cited

U.S. PATENT DOCUMENTS

| 5,752,973 | A |   | 5/1998  | Kieturakis |                        |
|-----------|---|---|---------|------------|------------------------|
| 5,964,697 | A | * | 10/1999 | Fowler, Jr.| A61B 17/0293           |
|           |   |   |         |            | 600/210                |
| 5,964,698 | A | * | 10/1999 | Fowler     | A61B 17/02             |
|           |   |   |         |            | 24/130                 |
| 6,117,072 | A | * | 9/2000  | Fowler, Jr.| A61B 17/0293           |
|           |   |   |         |            | 600/210                |
| 8,038,612 | B2|   | 10/2011 | Paz        |                        |
| 8,172,870 | B2|   | 5/2012  | Shipp      |                        |
| 8,262,567 | B2| * | 9/2012  | Sharp      | A61B 17/02             |
|           |   |   |         |            | 600/206                |
| 8,397,335 | B2|   | 3/2013  | Gordin et al.|                      |
| 8,945,155 | B2| * | 2/2015  | Gordin     | A61B 1/32              |
|           |   |   |         |            | 606/151                |
| 9,463,003 | B2|   | 10/2016 | Gordin et al.|                      |
| 10,143,459| B2|   | 12/2018 | Heftman    |                        |
| 2013/0137934 | A1 | | 5/2013 | Slaga et al. |                     |
| 2014/0235936 | A1 | | 8/2014 | Baas et al.  |                     |
| 2016/0220253 | A1 | | 8/2016 | Martinez et al. |                  |
| 2016/0317157 | A1 | | 11/2016| Bacher     |                        |

OTHER PUBLICATIONS

Fujii, T., et al., "A novel endoscopic suturing technique using a specially designed so-called "8-ring" in combination with resolution clips (with videos)", Gastrointestinal Endoscopy 66(6):1215-1220 (2007).
Matsumoto, K., et al., "T1594: A New Traction Device for Gastric Endoscopic Submucosal Dissecton (ESD): Two-Point Fixed by Latex Traction for Early Gastric Cancer", Gastrointestinal Endoscopy, 71(5):AB317 (2010).
Imaeda, H., et al., "Advanced endoscopic submucosal dissection with traction", World Journal of Gastrointestinal Endoscopy 6(7):286-295 (2014).
Sakamoto, N., et al.,"'Loop Clip' a new closure device for large mucosal defects after EMR and ESD", Endoscopy 40: E97-E98 (2008).
Fujihara, S., et al., "Management of a large mucosal defect after duodenal endoscopic resection", World Journal of Gastroenterology, 22(29):6595-6609 (2016).
Mori, H., et al., "The Loop Clip is Useful for Closing Large Mucosal Defects After Colorectal Endoscopic Submucosal Dissection: A Preliminary Clinical Study", Digestive Endoscopy 23:330-331 (2011).
Tsuji, K., et al., "Recent traction methods for endoscopic submucosal dissection", World Journal of Gastroenterology, 22(26):5917-5926 (2016).
Ritsuno, H., et al., "Prospective clinical trial of traction device-assisted endoscopic submucosal dissection of large superficial colorectal tumors using the S-O clip", Surgical Endoscopy 28:3143-3149 (2014).
Sakamoto, N., et al., "The facilitation of a new traction device (S-O clip) assisting endoscopic submucosal dissection for superficial colorectal neoplasms", Endoscopy, 40:E94-E95 (2008).
Takeda, T. et al., "Traction device to remove an adenoma in the appendiceal orifice by endoscopic submucosal dissection", Endoscopy 45:E239-E240 (2013).
Kato, M., et al., "Technical feasibility of line-assisted complete closure technique for large mucosal defects after colorectal endoscopic submucosal dissection", Endoscopy International Open, 5(1):E11-E16 (2017) DOI: http://dx.doi.org/10.1055/s-0042-121002.
International Search Report and Written Opinion for International Application No. PCT/US2019/029986, dated Oct. 17, 2019, 16 pages.

* cited by examiner

TISSUE RETRACTION DEVICE AND DELIVERY SYSTEM

CROSS-REFERENCE TO RELATED APPLICATIONS

This application claims the benefit of priority under 35 U.S.C. § 119 of U.S. Provisional Application No. 62/665,441, filed May 1, 2018, the entire disclosure of which is hereby incorporated by reference.

TECHNICAL FIELD

The present disclosure pertains to medical devices, and methods for manufacturing medical devices. More particularly, the present disclosure pertains to a tissue retraction device and related delivery system.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example tissue retraction device includes a first tissue engagement member coupled to an elastic member by a coupling assembly. The coupling assembly including a first coupler body having a first end region and a first compression member. Further, the first end region of the first coupler body is configured to extend into a portion of a lumen of the elastic member and the compression member is designed to compress the elastic member onto the first coupler body such that the elastic member is fixedly engaged with the coupler body.

Alternatively or additionally to any of the embodiments above, wherein the first end region of the first coupler body includes a channel extending around the circumference thereof.

Alternatively or additionally to any of the embodiments above, wherein the first compression member is designed to compress the elastic member into at least a portion of the channel of the first coupler body.

Alternatively or additionally to any of the embodiments above, wherein the compression member includes a compression ring.

Alternatively or additionally to any of the embodiments above, wherein the compression member includes a suture.

Alternatively or additionally to any of the embodiments above, wherein the coupling assembly further comprising a connection member, wherein the connection member is designed to couple the coupler body to the first tissue engagement member.

Alternatively or additionally to any of the embodiments above, wherein the connection member includes a post member and an attachment member, wherein a first end region of the post member is coupled to the attachment member, and wherein the post member is configured to extend through an aperture of the coupler body.

Alternatively or additionally to any of the embodiments above, wherein the post member further includes a second end region opposite the first end region, and wherein the first end region of the post member includes a first diameter, and wherein the second end region of the post member includes a second diameter larger than the first diameter.

Alternatively or additionally to any of the embodiments above, wherein the aperture includes a first inner diameter, and wherein the second diameter of the post member is larger than the first inner diameter of the aperture.

Alternatively or additionally to any of the embodiments above, wherein the first tissue engagement member includes a first tissue engagement portion and a first spring, and wherein the attachment member is designed to engage the first spring.

Alternatively or additionally to any of the embodiments above, wherein the attachment member is substantially C-shaped.

Alternatively or additionally to any of the embodiments above, wherein the attachment member includes a first fitting and a second fitting, and wherein the first fitting and the second fitting are designed to mate with one another.

Alternatively or additionally to any of the embodiments above, wherein the first fitting and the second fitting are designed to couple the first spring with the first end region of the post member.

Alternatively or additionally to any of the embodiments above, further comprising a second tissue engagement member, and wherein the elastic member extends between the first tissue engagement member and the second tissue engagement member.

Alternatively or additionally to any of the embodiments above, further comprising a tubular support member including a lumen extending therein, and wherein at least a portion of the elastic member extends within the lumen of the support member.

Alternatively or additionally to any of the embodiments above, wherein the support member is positioned between the first tissue engagement member and the second tissue engagement member.

Another tissue retraction device includes:
a first tissue clip coupled to an elastic member by a first coupling assembly, and a second tissue clip coupled to the elastic member by a second coupling assembly, and wherein the first and second coupling assemblies each include:
a coupler body having a first end region; and
a compression member;
wherein the first end region of each of the coupler bodies is configured to extend into a portion of the lumen of the elastic member;
wherein each of the compression members are designed to compress the elastic member onto each of the coupler bodies such that the elastic member is fixedly engaged to each of the coupler bodies.

Alternatively or additionally to any of the embodiments above, wherein the first end region of the each of the coupler bodies includes a channel extending around the circumference thereof.

Alternatively or additionally to any of the embodiments above, wherein each of the compression members is designed to compress the elastic member within at least a portion of the channel of each of the coupler bodies.

A method of dissecting tissue includes:
advancing a tissue retraction device to a target site, the tissue retraction device including:

a first tissue engagement member coupled to an elastic member by a coupling assembly, the coupling assembly including:
   a first coupler body having a first end region; and
   a first compression member;
wherein the first end region of the first coupler body is configured to extend into a portion of a lumen of the elastic member;
wherein the compression member is designed to compress the elastic member onto the first coupler body such that the elastic member is fixedly engaged with the coupler body;
manipulating the first tissue engagement member between a first configuration and a second open configuration; and
   attaching the first tissue engagement member to the target site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
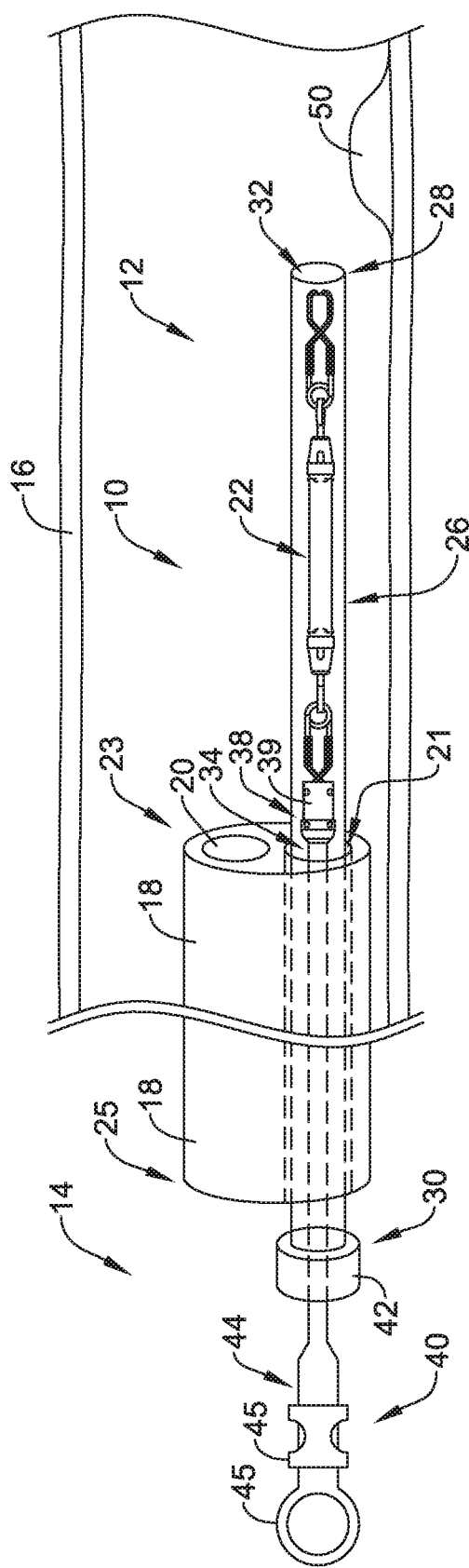
FIG. 1 is a partial cross-sectional side view of an example tissue retraction device positioned within a body lumen.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, including intravascular procedures, procedures along the digestive and/or biliary tract, thoracic procedures, etc. utilize medical devices to access tissue intended for removal (e.g., "target tissue") within the body. For example, in some current medical procedures (e.g., Endoscopic Submucosal Dissection (ESD), Peroral Endoscopic Myotomy (POEM), cholecystectomy, Video-Assisted Thoracoscopic Surgery (VATS)), physicians may utilize an endoscope or similar medical device to access and remove cancerous lesions. Further, as part of the procedure, the physician may utilize an endoscope capable of both accessing the target tissue site while also permitting a cutting device to be deployed therethrough to excise the target tissue. Additionally, in some instances, the endoscope may incorporate features which assist the physician in visualizing and performing the tissue dissection procedure. For example, some endoscopes may include a light and/or camera designed to illuminate the body lumen as the scope is navigated and positioned adjacent to the target tissue site. Additionally, some endoscopes may also include a lumen (e.g., a working channel) through which a cutting member or other accessory medical devices may be deployed and utilized.

While physicians are becoming more proficient at extracting cancerous lesions from within the body (e.g., within the digestive tract, abdominal cavity, thoracic cavity, etc.), the extraction methods continue to be inefficient and time-consuming. For example, in some instances poor visualization of the tissue dissection process may result in a prolonged tissue dissection procedure. In another example, the actual tissue that the physician is attempting to dissect may, itself, obstruct the pathway of the tools which the physician is using during the procedure. Therefore, in some instances it may be desirable to utilize a medical device which assists in improving the visualization of the target tissue while also mitigating the obstruction of dissection tools the physician is utilizing. Therefore, in some instances it may be desirable to utilize a tissue retraction device which lifts and retracts the region of tissue to be dissected by the physician. Disclosed herein are medical devices such as a tissue retraction device and delivery system that are designed to lift and retract the target tissue.

FIG. 1 is a partial cross-sectional side view of an example tissue retraction delivery system 10 including a distal portion 12 and a proximal portion 14. FIG. 1 shows the distal portion 12 of the tissue retraction system 10 positioned within an example body lumen 16. Further, FIG. 1 shows that the proximal portion 14 of the tissue retraction system 10 may extend out of the body lumen 16 to a position outside the body. As shown in FIG. 1, the tissue retraction system may include a tissue retraction device 22. Additionally, the tissue retraction system 10 may include a delivery catheter 26. The delivery catheter 26 may be constructed from a semi-rigid or compliant material such as a thermoplastic elastomer, silicone rubber, nylon, polyurethane, polyethylene terephthalate (PET), latex, or similar materials. The delivery catheter 26 may have a distal end region 28 and a proximal end region 30. Further, a lumen 32 may extend through the delivery catheter 26 from proximal end region 30 to the distal end region 28. As illustrated, the tissue retraction device 22 may be positioned along the distal end region 28 and within the lumen 32 of the delivery catheter 26.

Additionally, FIG. 1 illustrates that the delivery catheter 26 (including the tissue retraction device 22) may extend through an example medical device 18. As discussed above, in FIG. 1 the medical device 18 may take the form of an endoscope, laproscope, needle, catheter, guide tube, or the like. The medical device 18 may include a distal portion 23 and a proximal portion 25. Further, FIG. 1 illustrates that the distal portion 23 of the medical device 18 may be advanced within a portion of a body lumen 16 to a position adjacent a target tissue 50, such as a lesion, while the proximal portion 25 of the medical device 18 may extend out of the body lumen 16 to a position outside the body.

Medical device 18 may include a lumen 21 extending from the proximal portion 25 to the distal portion 23 of the medical device 18. In some examples, the lumen 21 may be referred to as the "working channel" of the medical device 18. The lumen 21 may be designed to permit a variety of medical devices to pass therethrough. For example, a physician may pass or exchange a variety of medical devices through the working channel 21 over the course of a given medical procedure. For example, as illustrated in FIG. 1, the delivery catheter 26 (including the tissue retraction device 22) may extend through the lumen 21 of the medical device 18. In other words, FIG. 1 illustrates that a physician may insert the distal end 28 of the delivery catheter 26 into the proximal portion 25 of the medical device 18 (which is outside the body), advance the delivery catheter 26 through the lumen 21 whereby the distal end 28 of the delivery catheter may eventually extend out of the distal portion 23 of the medical device 18 to a position adjacent the target tissue 50.

The proximal end 30 of the delivery catheter 26 may include a control member 42. The control member 42 may be utilized as a grip to control the translation of the delivery catheter 26. Further, the control member 42 may also permit a user to rotate the delivery catheter 26. As will be described in greater detail below, the control member 42 may be utilized by a physician to advance the distal end 28 of the delivery catheter 26 to a position adjacent a target tissue 50 prior to deploying the tissue retraction device 22 from the distal end 28 of the delivery catheter 26.

In some examples, the medical device 18 may include additional features. For example, the medical device 18 shown in FIG. 1 may include an accessory feature 20 (e.g., light, camera, etc.) positioned on the distal portion 23 of the medical device 18. Further, other medical devices 18 having additional features may be utilized in conjunction with the tissue retraction system 10.

As illustrated in FIG. 1, in some examples the tissue retraction system 10 may include a manipulating device 34 ("manipulator") designed to advance (e.g., push, deploy, etc.) the tissue retraction device 22 out of the distal end 28 of the delivery catheter 26. As will be described in greater detail below, once the manipulator 34 has pushed the tissue retraction device 22 out of the delivery catheter 26, it may also be used to position and/or manipulate the tissue retraction device 22 within the body lumen 16.

As shown in FIG. 1, the manipulator 34 may extend within the lumen 32 of the delivery catheter 26. In other words, FIG. 1 illustrates that a distal end 38 of the manipulator 34 may extend from the proximal end 30 of the delivery catheter 26 (which is outside the body), through the lumen 32 of the delivery catheter 26 whereby the distal end 38 of the manipulator 34 may be positioned adjacent the proximal end of the tissue retraction device 22.

The proximal end 40 of the manipulator 34 may include a handle member 44. Handle member 44 may include one or more finger grips 45 which permit a user to grasp and thereby advance (e.g., translate) the distal end 38 of the manipulator within the lumen 32 of the delivery catheter 26. In other words, by grasping and manipulating the handle 44, a user may be able to translate the manipulator 34 along the longitudinal axis of the delivery catheter 26. The handle design illustrated in FIG. 1 is a schematic. Other handle designs are contemplated. For example, handle designs that include different grip arrangements, ergonomic features, etc. that may be utilized with the tissue retraction system 10 (and components thereof) described herein are contemplated.

The distal end 38 of the manipulator 34 may include a grasping member 39 (e.g., forceps, jaws, etc.). When positioned within the lumen 32 of the delivery catheter 26, the grasping member 39 may be in a closed position (e.g., the jaws of the grasping member 39 may be closed and contacting one another). Further, the handle member 44 may be designed to control the opening and/or closing of the grasping member 39. In other words, when the grasping member 39 is advanced to a position outside of the lumen 32 of the delivery catheter 26, a user may manipulate the handle member 44 to open and/or close the grasping member 39.

As described above, the manipulator 34 may be utilized to deploy the tissue retraction device 22 out of the distal end 28 of the delivery catheter 26. Specifically, it can be appreciated that, when positioned adjacent to tissue target 50, a user may advance the manipulator 34 in a proximal-to-distal direction within the lumen 32 of the delivery catheter 26 such that the grasping member 39 may contact and push the proximal end of the tissue retraction device 22 out of the distal end 28 of the delivery catheter 26.

In at least some examples contemplated herein, the manipulator 34 and the tissue retraction device 22 may be positioned within the delivery catheter 26 as depicted in FIG. 1 prior to the delivery catheter 26 being advanced through the lumen 21 of the medical device 18. In other words, in some examples, both the manipulator 34 and the tissue retraction device 22 may be "pre-loaded" into the delivery catheter 26 prior to being inserted and advanced through the working channel 21 of the medical device 18 to a position adjacent to target tissue 50. In other examples, however, only the tissue retraction device 22 may be pre-loaded into the delivery catheter 26 and advanced within the lumen 21 of the medical device 18 to a position adjacent to target tissue 50, after which the manipulator 34 may be separately inserted into the lumen 21 of the medical device 18 and advanced to a position in which grasping member 39 is adjacent and/or contacting the proximal end of the tissue retraction device 22.

It can be appreciated from the above discussion that the tissue retraction system 10 may be designed such that the delivery catheter 26 and the manipulator 34 may be moved (e.g., translated, rotated, etc.) relative to one another. For example, once the distal end 28 of the delivery catheter 26 is positioned adjacent to the target tissue 50 (with the manipulator 34 positioned adjacent to the distal end of the tissue retraction device 22), a user may grasp both the control member 42 and the handle member 44. This may permit the user to maintain the distal end 28 of the delivery catheter 26 in a fixed position while advancing the manipulator 34 in a distal direction such that the grasping member 39 moves distally relative to the distal end 28 of the delivery catheter 26. It can be appreciated that this relative movement may push the tissue retraction device 22 out of the distal end 28 of the delivery catheter 26.

In other examples, it can be appreciated that instead of a user advancing the manipulator 34 in a distal direction to deploy the tissue retraction device 22, the user may, alternatively, retract the delivery catheter 26 while maintaining the manipulator 34 in a fixed position. The retraction of the delivery catheter 26 may "uncover" the tissue retraction device 22, thereby releasing it from the lumen 32 of the delivery catheter 26.

Figure 2:
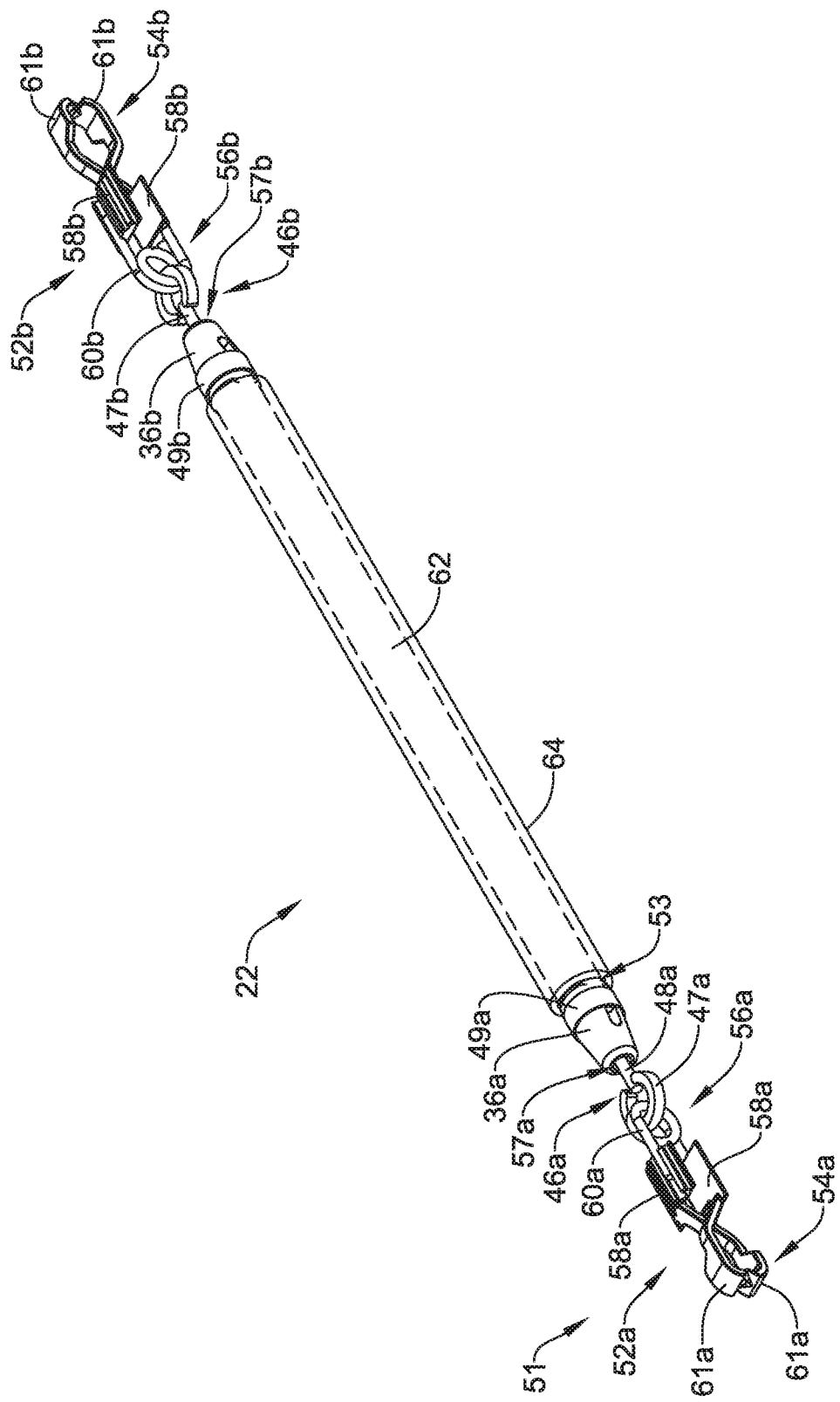
FIG. 2 is a perspective view of an example tissue retraction device.

FIG. 2 illustrates an example tissue retraction device 22. The tissue retraction device 22 may include one or more engagement members 51 (e.g., clip, clasp, fastener, clamp, etc.). For example, FIG. 2 illustrates that the tissue retraction device 22 may include a first engagement member 52a and a second engagement member 52b. The first engagement member 52a may include a first end 54a and a second end 56a. The first end 54a may include one or more jaws 61a (e.g., end effectors). The jaws 61a may be designed such that they move relative to one another. FIG. 2 further illustrates that the second end 56a of the first engagement member 52a may include a spring 60a. It can be appreciated that the spring 60a may be designed to provide a compressive force that is translated through the body of the first engagement member 52a to the jaw members 61a, thereby biasing the jaw members 61a in a closed position (e.g., a position in which the jaw members 61a are contacting one another).

In some examples, the ends of the jaw members 61a may not necessarily contact one another while in a closed position. The jaw members 61a may be spaced apart from one another while in a closed position. Spacing the jaw members 61a apart from one another while in a closed position may permit additional compressive force to be generated when in contact with tissue. This additional compressive force could be termed "preload." The range of preload forces could vary from about 5 grams of force to about 200 grams of force, or about 15 grams of force to about 40 grams of force.

It can be appreciated that the engagement members 51 depicted in the examples disclosed herein are schematic. In other words, it is contemplated that the engagement members 51 described herein may include alternative design arrangements, features, geometries etc. without departing from the scope of the examples contemplated herein. For example, it is contemplated that the spring 60a of the first engagement member 52a may be positioned between the first end 54a and the second end 56a of the first engagement member 52a). Additionally, it is contemplated that the jaws (e.g., end effectors) may have a variety of different shapes and/or geometries without departing from the scope of the examples contemplated herein. Other variations are contemplated.

FIG. 2 further illustrates that the first engagement member 52a may include one or more gripping members 58a. For example, FIG. 2 illustrates that the gripping member 58a may be formed from the same material as the jaw member 61a. In other words, the jaw 61a and the gripping member 58a may be formed as a monolithic component. For example, the jaws 61a (e.g., end effectors) and the gripping members may be metal injection molded (MIM), conventionally machined, stamped, additive manufactured or the like. However, this is not intended to be limiting. Rather, it is contemplated that the jaw 61a and the gripping member 58a may be formed as two separate components which are attached (e.g., welded, glued, press fit, etc.) together to form the structure shown in FIG. 2. Additionally, FIG. 2 illustrates that, in some examples, a portion of the gripping member 58a may be designed to engage, mate, interconnect, attached to, etc. the spring 60a. For example, FIG. 2 illustrates a portion of the spring 60a extending into a channel of the gripping member 58a. The spring 60a may be rigidly attached (e.g., weld, affixed, etc.) to the gripping member 58a.

As described above, after the tissue retraction device 22 has been deployed out of the distal end 28 of the delivery catheter 26, the manipulator 34 may be utilized to position and/or attach the tissue retraction device 22 to the target tissue 50 within body lumen 16. It can be appreciated that the gripping members 58a may be designed to engage the grasping member 39 (located on the distal end 38 of the manipulator 34). In other words, the gripping members 58a may provide an interface for which the grasping member 39 may engage, attach, grip, grab, capture, etc. the first engagement member 52a.

Furthermore, the gripping members 58a may be designed such that they permit the manipulator 34 to efficiently acquire, position (and/or reposition), and open/close the jaws 61a of the first engagement member 52a. While FIG. 2 depicts the gripping members 58a positioned between the first end 54a and/or the second end 56a of first engagement member 52a, it is contemplated that the gripping members 58a may be located along other portions of first engagement member 52a. For example, the gripping members 58a may be positioned on the first end 54a and/or the second end 56a of first engagement member 52a.

As discussed above, the tissue retraction device 22 may include more than one tissue engagement member (e.g., another engagement member in addition to the first tissue engagement member 52a described above). For example, FIG. 2 illustrates that the tissue retraction device 22 may include a second tissue engagement member 52b. The second tissue engagement member 52b may be similar in form and function to the first tissue engagement member 52a. For example, the second tissue engagement member 52b may include a first end 54b and a second end 56b. The first end 54b may include one or more jaws 61b. The jaws 61b may be designed such that they move relative to one another. FIG. 2 further illustrates that the second end 56b of the second tissue engagement member 52b may include a spring 60b. It can be appreciated that the spring 60b may be designed to provide a compressive force that is translated through the body of the second engagement member 52b to the jaw members 61b, thereby biasing the jaw members 61b in a closed position (e.g., a position in which the jaw members 61b are contacting one another). It can be appreciated that the second engagement member 52b depicted in the examples disclosed herein is schematic. In other words, it is contemplated that the second engagement member 52*b* described herein may include alternative design arrangements, features, geometries, etc. without departing from the scope of the examples contemplated herein. For example, it is contemplated that the spring 60*b* of the second engagement member 52*b* may be positioned between the first end 54*b* and the second end 56*b* of the second engagement member 52*b*). Other variations are contemplated.

FIG. 2 further illustrates that the first engagement member 52*a* may include one or more gripping members 58*b*. For example, FIG. 2 illustrates that the gripping member 58*b* may be formed from the same material as the jaw member 61*b*. In other words, the jaw 61*b* and the gripping member 58*b* may be formed as a monolithic component. For example, the jaws 61*a* (e.g., end effectors) and the gripping members may be metal injection molded (MIM), conventionally machined, stamped, additive manufactured or the like. However, this is not intended to be limiting. Rather, it is contemplated that the jaw 61*a* and the gripping member 58*a* may be formed as two separate components which are attached (e.g., welded, glued, press fit, etc.) together to form the structure shown in FIG. 2. Additionally, FIG. 2 illustrates that, in some examples, a portion of the gripping member 58*b* may be designed to engage, mate, interconnect, attached to, etc. the spring 60*b*. For example, FIG. 2 illustrates a portion of the spring 60*b* extending into a channel of the gripping member 58*b*. The spring 60*b* may be rigidly attached (e.g., weld, affixed, etc.) to the gripping member 58*b*.

FIG. 2 further illustrates that the tissue retraction device 22 may include one or a tether 62 (depicted as the dashed line in FIG. 2) coupled to the first engagement member 52*a*, the second engagement member 52*b* or both the first engagement member 52*a* and the second engagement member 52*b*. The tether 62 may be a tubular member having a lumen extending therein. The tether 62 may be referred to as an elastic member, band, rope, cord, leash, strap, strand, etc. The tether 62 may include a variety of cross-sectional geometries. For example, the tether may be circular, rectangular, triangular, or the like. Further, the tether 62 may be bioabsorbable.

In at least some examples, the tether 62 may be elastomeric. In some examples, the tether 62 may be constructed from an elastomeric material such as latex, Nitrile® rubber, ethylene propylene diene rubber, silicone rubber, chloroprene, polychloroprene (e.g., Neoprene®), polyolefin, thermoplastic elastomer, polyisoprene, etc.

The tether member 62 may elongate from a first, unelongated (e.g., relaxed) position to a second, elongated position. It can be appreciated that when the tissue retraction device 22 is in an elongated position, the tissue elongation device is in tension, and therefore includes a retraction force which is pulling the first engagement member 52*a* toward the second engagement member 52*b* along the longitudinal axis of the tissue retraction device 22.

As described above, prior to being deployed from the delivery catheter 26, the tissue retraction device 22 may be positioned in an unelongated, relaxed state within the distal end 28 of the delivery catheter. Furthermore, proper alignment of the tissue retraction device 22 within the delivery catheter 26 (prior to deployment) must be maintained to ensure that the tissue retraction device 22 is efficiently deployed within the body lumen 16. For example, it is important to prevent the tissue retraction device 22 from folding and/or wrapping upon itself (e.g., folding back on itself) while being advanced and/or manipulated within the distal end 28 of the delivery catheter 26.

FIG. 2 illustrates that in some examples, the tissue retraction device 22 may include a support member 64. In some instances, the support member 64 may be a tubular member having a lumen 53 extending therein. For example, the tissue retraction device 22 shown in FIG. 2 illustrates the tether member 62 extending within the lumen 53 of the support member 64. Additionally, FIG. 2 illustrates that the support member 64 may extend between (e.g., be positioned between) the first tissue engagement member 52*a* and the second tissue engagement member 52*b*. While FIG. 2 depicts the support member 64 as a tubular member, other cross-sectional shapes of support member 64 are contemplated. For example, the cross-sectional shape of the support member 64 may be rectangular, triangular, ovular, square, or the like. Additionally, it is contemplated that the tissue retraction device 22 may include more than one support member 64. For example, the tissue retraction device 22 may include 1, 2, 3, 4 or more support members.

As described above, FIG. 2 shows that the support member 64 may be disposed along the tether member 62. For example, in some examples the tether member 62 may extend through the lumen 53 of the support member 64. In at least some examples, the support member 64 may permit the tether 62 to compress into the lumen 53 of the support member 64. Therefore, diameter of the lumen 53 of the support member 64 may be wide enough to permit the tether 62 to curl upon itself to be "stored" within the lumen of the support member 64. Allowing the tether 62 to be stored within the lumen of the support member 64 may prevent the tether 62 from being entangled with the first engagement member 52*a*.

Additionally, in at least some examples described herein, the support member 64 may include sufficient stiffness and column strength to withstand compression during packaging and storage prior to device delivery. Possible materials include polypropylene, PET, thermoplastic elastomers (TPE), polyethylene (PE), or high density polyethylene (HDPE) such as Celanese GUR HOSTALLOY 731.

FIG. 2 further illustrates that the tether 62 may be coupled to the tissue engagement member 52*a* via a coupler body 36*a* and a connection member 46*a*. As will be described in greater detail below, the connection member 46*a* may include a post member 48*a* and an attachment member 47*a*. FIG. 2 further illustrates that a proximal end of the coupler body 36*a* may extend within the lumen 53 of the tether member 62. A compression member 49*a* may be positioned overtop both the proximal end of the coupler body 36*a* and the tether 62, whereby the compression member 49*a* may radially compress the tether 62 onto the proximal end of the coupler body 36*a* with sufficient force to fixedly attach the tether 62 to the coupler body 36*a*. In other words, the tether 62 may be attached to the coupler body 36*a* by "sandwiching" the tether 62 between the coupler body 36*a* and the compression 49*a*. The compression member 49*a* may include a variety of different structures without departing from the scope of the examples contemplated herein. For example, the compression member 49*a* may include a compression ring, a suture, a clamp, a string, a knot, a crimped ultrasonic weld, a loop, etc.

As will be described in greater detail below, the post member 48*a* may extend through an aperture 57*a* formed in the coupler body 36*a*, whereby a proximal end of the post member 48*a* may be prevented from being pulled through the aperture 57*a*. In other words, as will be illustrated in FIG. 3 below, the post member 48*a* may include a proximal end which is designed to allow the post member 48a to rotate while preventing the post member 48a from separating from the coupler body 36a.

Additionally, FIG. 2 illustrates that the distal end of post member 48a may be attached to the attachment member 47a. For example, FIG. 2 illustrates that the attachment member 47a may include a curved portion (e.g., a substantially C-shaped portion), which may resemble a partial ring. FIG. 2 further illustrates that the attachment member 47a may extend through the looped portion of the spring 60a, thereby coupling the attachment member 47a to the tissue engagement member 52a via the spring 60a. Additionally, FIG. 2 illustrates that the attachment member 47a may be attached to the distal end of the post member 48a, thereby coupling the attachment member 47a to the coupler body 36a via the post member 48a. It can be appreciated, therefore, that the connection member 46a (which includes the attachment member 47a and the post member 48a) together with the coupler body 36a and the compression ring 49a, may couple the tissue engagement member 52a to the tether member 62.

It is noted that be above description my also apply to coupling the second tissue engagement member 52b with the tether 62. For example, the second tissue engagement member 52b may be coupled to a coupler body 36b via a connection member 46b. Similar to that described above, the connection member 46b may include an attachment member 47b and a post member 48b. The attachment member 47b may be coupled to the spring 60b. Additionally, the attachment member 47b may be attached to the post member 48b. The post member 48b may extend through an aperture 57b (not visible in FIG. 2) in the coupler body 36b, as described above. Further, the tether 62 may be attached to the coupler body 36b via radial compression of the compression ring 49b onto the coupler body 36b.

Figure 3:
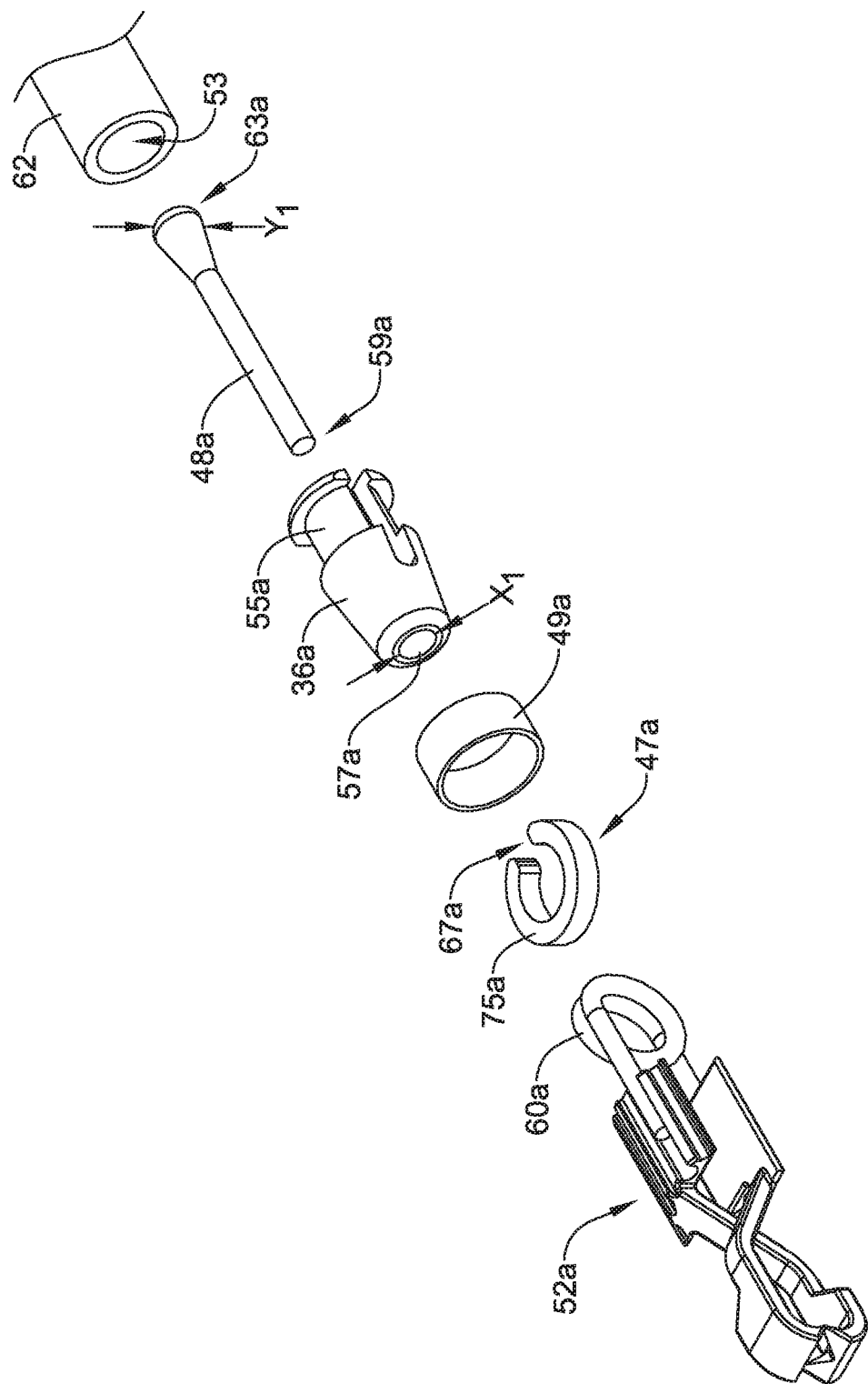
FIG. 3 is an exploded view of the example tissue retraction device shown in FIG. 2.

FIG. 3 is an exploded view of one end of the tissue retraction device 22 described above. FIG. 3 illustrates the individual components utilized to couple the tether member 62 to the tissue engagement member 52a, as described above. For example, FIG. 3 illustrates the tissue engagement member 52a, which includes spring 60a. As shown in FIG. 3, the spring 60a may include a coiled portion through which the attachment member 47a may extend. As described above and further illustrated in FIG. 3, the attachment member 47a may include a curved portion 75a which resembles a partial ring. Additionally, the attachment member 47a may include an opening 67a which, for purposes of assembly, may permit the attachment to be inserted into the coiled portion of the spring 60a.

FIG. 3 further illustrates both the compression member 49a and the coupler body 36a. In some examples the coupler body 36a may include a channel 55a which extends circumferentially around the coupler body 36a. The channel 55a may be designed to mate with the compression member 49a. For example, the width, depth and/or profile of the channel 55a may mate with the width, thickness and/or profile of the compression member 49a. As described above, the tether 62 may be radially compressed between the coupler body 36a and the compression member 49a to fixedly attach the tether 62 to the coupler body 36a.

Additionally, FIG. 3 illustrates that the coupler body 36a may include an aperture 57a through which the post member 48a may extend. The diameter of the aperture 57a is depicted as "$X_1$" in FIG. 3. Additionally, FIG. 3 illustrates that the post member 48a may include a first end region 59a and a second end region 63a. The second end region 63a of the post member 48a may include a tapered portion. The tapered portion may include a diameter "$Y_1$" which is greater than the diameter $X_1$ of the aperture 57a. It can be appreciated that the post member 48a may include a length which permits the post member 48a to extend through the aperture 57a whereby the first end region 59a may be fixedly attached to the attachment member 47a. For example, the first end region 59a of the post member 48a may be welded to the attachment member 47a. It can further be appreciated that after the post member 48a is extended through the coupler body 36a and attached to the attachment member 47a, the coupler body 36a may be coupled to the attached combination of the attachment member 47a and the post member 48a.

FIG. 3 further illustrates that the lumen 53 of the tether 62 may be sized such that it may be positioned over a portion of the coupler body 36a. For example, the tether 62 may be positioned overtop the proximal portion of the coupler body 36a such that a portion of the tether 62 may be positioned along the channel 55a. As described above, the compression member 49a may be positioned overtop the tether 62 such that it radially compresses the tether 62 onto the coupler body 36a, thereby attaching the tether 62 to the coupler body 36a.

Figure 4:
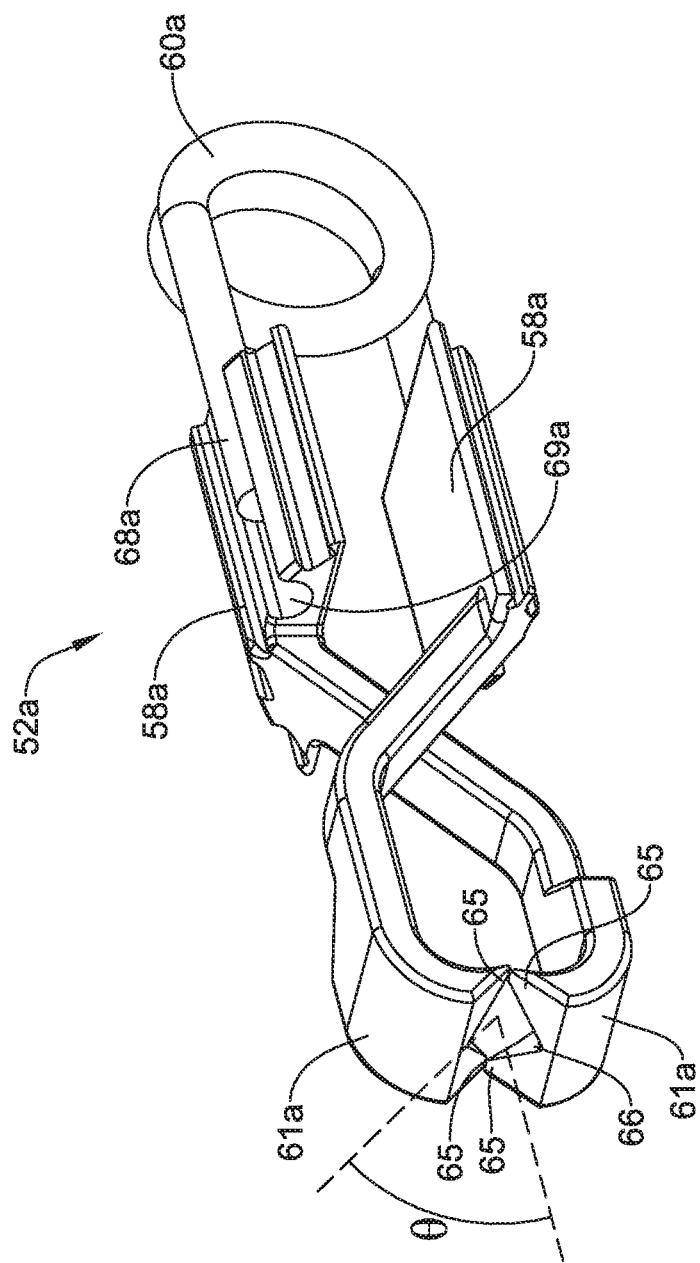
FIG. 4 illustrates an example tissue engagement member.

FIG. 4 illustrates an example tissue engagement member 52a. As discussed above, the tissue engagement member 52a may include a jaw members 61a, gripping members 58a and a coiled spring 60a. FIG. 4 further illustrates that the spring portion 60a may include one or more stems 68a that engage (e.g., mate) with a groove portion 69a located in the gripping member 58a. It is contemplated that the stems 68a may be attached within the groove 69a with a variety of techniques. For example, the stem 68a may be welded, press fit, glued, etc. within the groove portion 69a.

Additionally, FIG. 4 illustrates that the jaws 61a may each include one or more teeth 65. It can be appreciated that the teeth 65 may include a variety of different of shapes which are oriented in a variety of different configurations. Each jaw 61a illustrated in FIG. 4 may include two teeth 65, wherein the teeth 65 of one jaw 61a may mirror the teeth 65 of the other jaw 61a. In other words, the teeth 65 of the "top" jaw may be aligned with the teeth 65 of the "bottom" jaw. Further, FIG. 4 illustrates that the particular arrangement of the teeth results in an aperture 66 located in a central region of the teeth 65. Furthermore, it can be appreciated that the jaws 61a may be designed to exhibit a slope facing the coiled portion 60a of the first engagement member 52a. For example, FIG. 4 illustrates that the "face" of each jaw 61a defining each of the teeth 65 may be sloped inward at an angle, depicted as "θ" in FIG. 4. FIG. 4 illustrates that the angle may create a sharp point that may engage tissue more aggressively. The direction of the slope enhances tissue engagement by discouraging captured tissue from disengaging.

Figure 5:
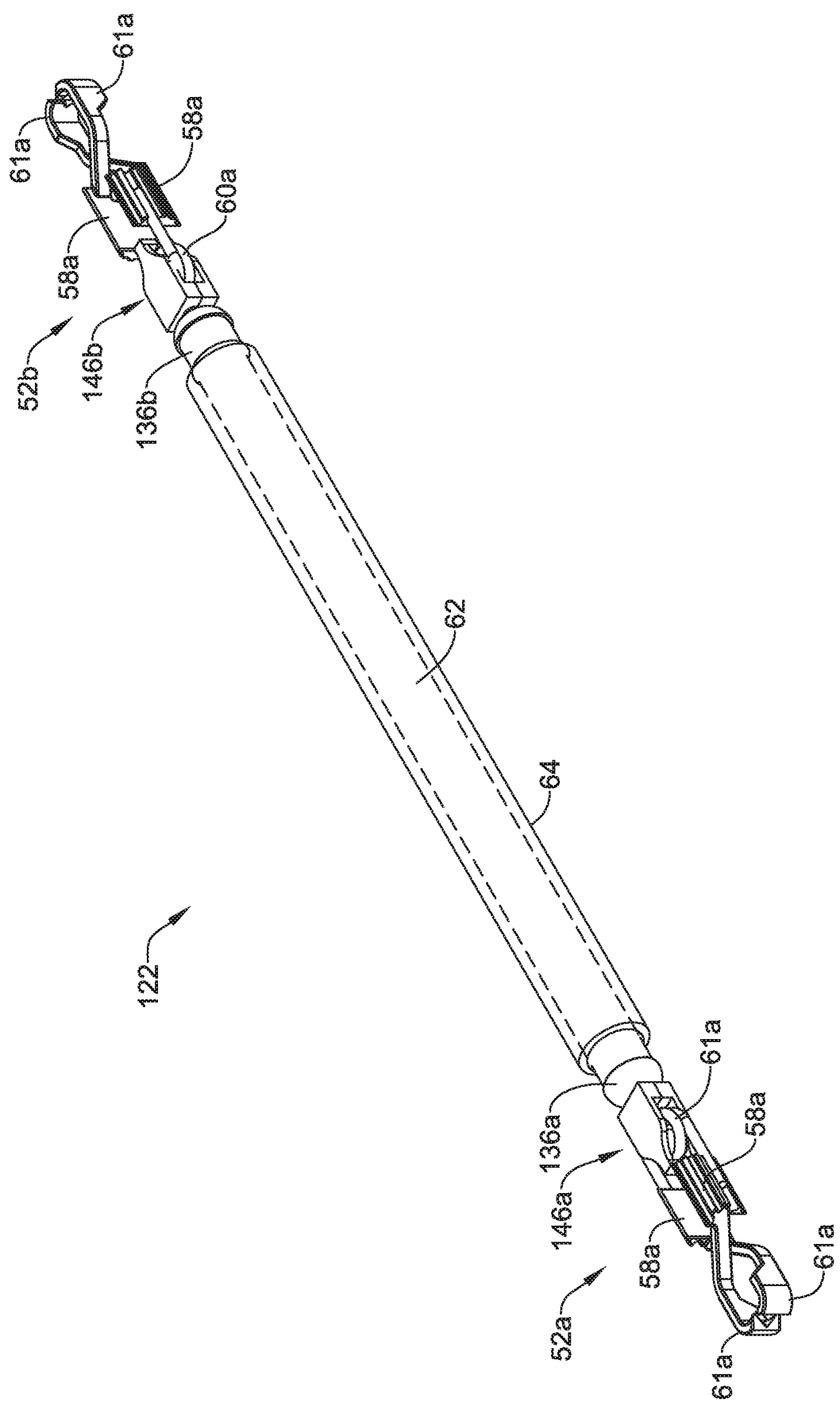
FIG. 5 is a perspective view of another example tissue retraction device.

FIG. 5 illustrates another example tissue retraction device 122. The tissue retraction device 122 may be similar in form and function to the tissue retraction device 22 described above. For example, the tissue retraction device may include a first tissue engagement member 52a (including jaws 61a, gripping members 58a and spring 60a) and a second tissue engagement member 52b ((including jaws 61b, gripping members 58b and spring 60b). Additionally, the first tissue engagement member 52a may be coupled to a tether 62 via a connection member 146a and a coupler body 136a. Similarly, the second tissue engagement member 52b may be coupled to the tether 62 via a connection member 146b and a coupler body 136b. As discussed above, the tissue retraction device 122 may include a support member 64 disposed along the tether 62.

Figure 6:
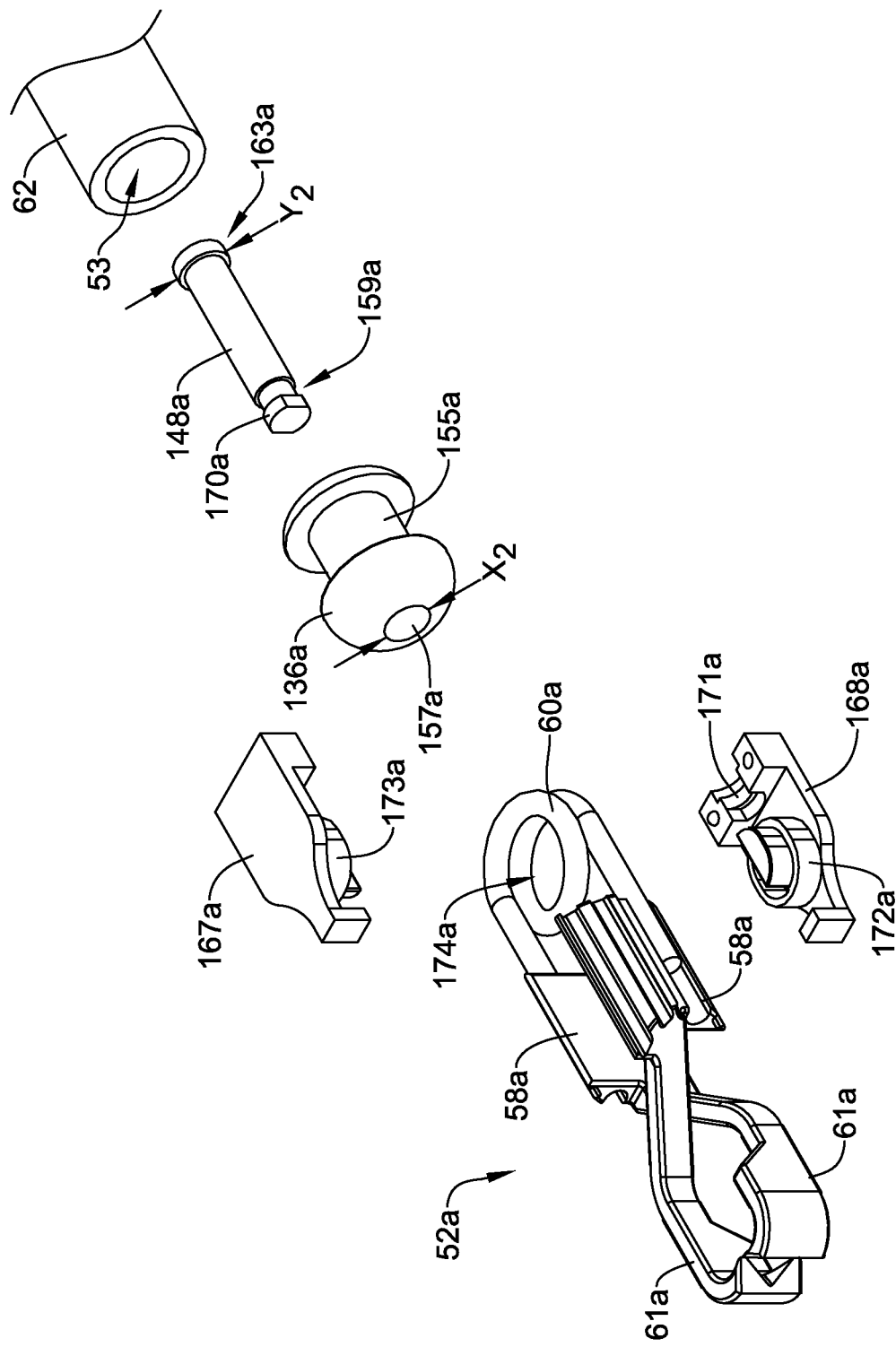
FIG. 6 is an exploded view of the example tissue retraction device shown in FIG. 5.

FIG. 6 is an exploded view of one end of the tissue retraction device 122 described above. Similar to that described above with respect to FIG. 3, FIG. 6 illustrates the individual components utilized to couple the tether 62 to the tissue engagement member 52a shown in FIG. 5. For example, FIG. 6 illustrates the tissue engagement member 52a, which includes the gripping members 58a and the spring 60a. Additionally, FIG. 6 illustrates the tether 62 including the lumen 53 extending therein. However, FIG. 6 further illustrates the individual components of the connection member 146a (described in FIG. 5) and which, in conjunction with the coupler body 136a, couple the tissue engagement member 52a with the tether 62.

To that end, the connection member 146a (described in FIG. 5) may include a post member 148a, a first fitting 167a and a second fitting 168a. The post member may include a first end 159a and a second end 163a. It can be appreciated that the first fitting 167a and the second fitting 168a may be designed to mate with one another. In other words, the first fitting 167a and the second fitting 168a may be two separate components which "snap" together to form a single component. Additionally, it can be further appreciated that the first fitting 167a and the second fitting 168a may include one or more "voids" or "protrusions" which are designed to capture both the coiled portion of the spring 60a and a projection 170a located on the first end 159a of the post member 148a.

For example, the projection 170a may be designed to engage a void 171a, half of which is formed in the first fitting 167a and half of which is formed in the second fitting 168a (it is noted that the half of the void 171a formed in the first fitting 167a cannot be seen in FIG. 6). Additionally, FIG. 6 illustrates a first protrusion 172a extending outward from the second fitting 168a which is designed to mate with a second protrusion 173a extending outward from the first fitting 167a. As discussed above, the first protrusion 172a and the second protrusion 173a may be designed to interlock within one another through an opening 174a formed in the spring portion 60a, thereby capturing the spring portion 60a between the first fitting 167a and a second fitting 168a.

Additionally, FIG. 6 illustrates that the coupler body 136a may include an aperture 157a through which the post member 148a may extend. The diameter of the aperture 157a is depicted as "$X_2$" in FIG. 6. Additionally, FIG. 6 illustrates that the post member 148a may include a first end region 159a and a second end region 163a. The second end region 163a of the post member 148a may include an enlarged portion. The enlarged portion may include a diameter "$Y_2$" which is greater than the diameter $X_2$ of the aperture 157a. It can be appreciated that the post member 148a may include a length which permits the post member 148a to extend through the aperture 157a, whereby the projection 170a of the first end region 159a may be fixedly attached with the void 171a formed via the first fitting 167a and the second fitting 168a. It can further be appreciated that after the post member 148a is extended through the coupler body 136a and attached to the first fitting 167a and the second fitting 168a, the coupler body 136a may be coupled to the attached combination of the first fitting 167a, the second fitting 168a and the post member 148a.

FIG. 6 further illustrates that the lumen 53 of the tether 62 may be sized such that it may be positioned over a portion of the coupler body 136a. For example, the tether 62 may be positioned overtop the proximal portion of the coupler body 136a such that a portion of the tether 62 may be positioned along a channel 155a (extending circumferentially around the coupler body 136a). As described above, a compression member (e.g., compression ring, suture, band, clamp, etc.) may be positioned overtop the tether 62 such that it radially compresses the tether 62 onto the coupler body 136a, thereby attaching the tether 62 to the coupler body 136a.

Figure 7:
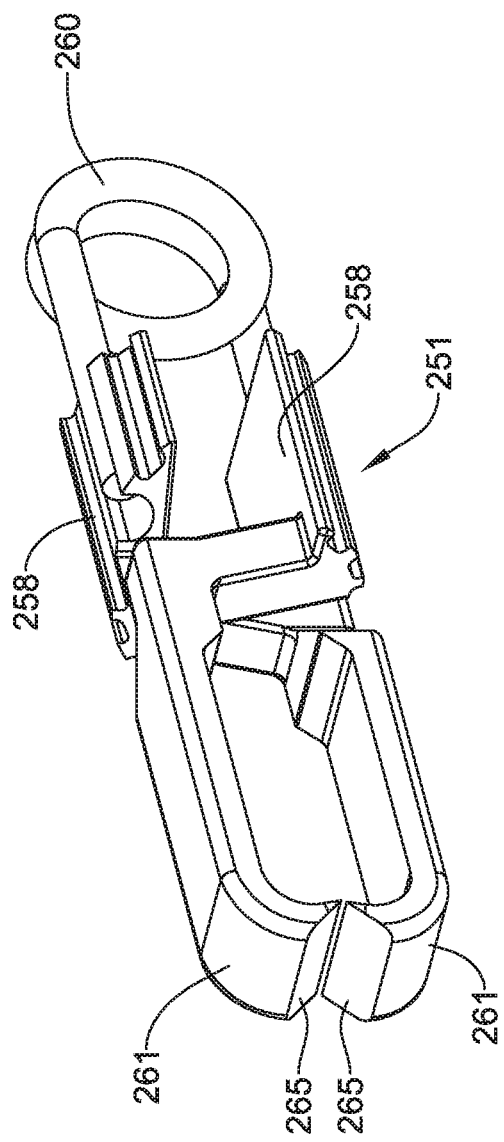
FIGS. 7-9 illustrate example tissue engagement members.
Figure 8:
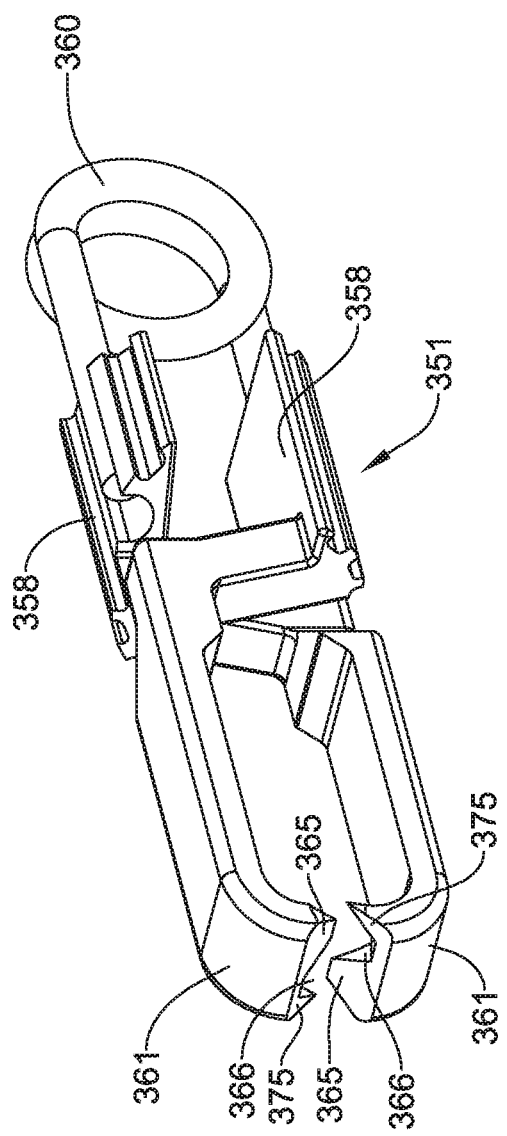
Figure 9:
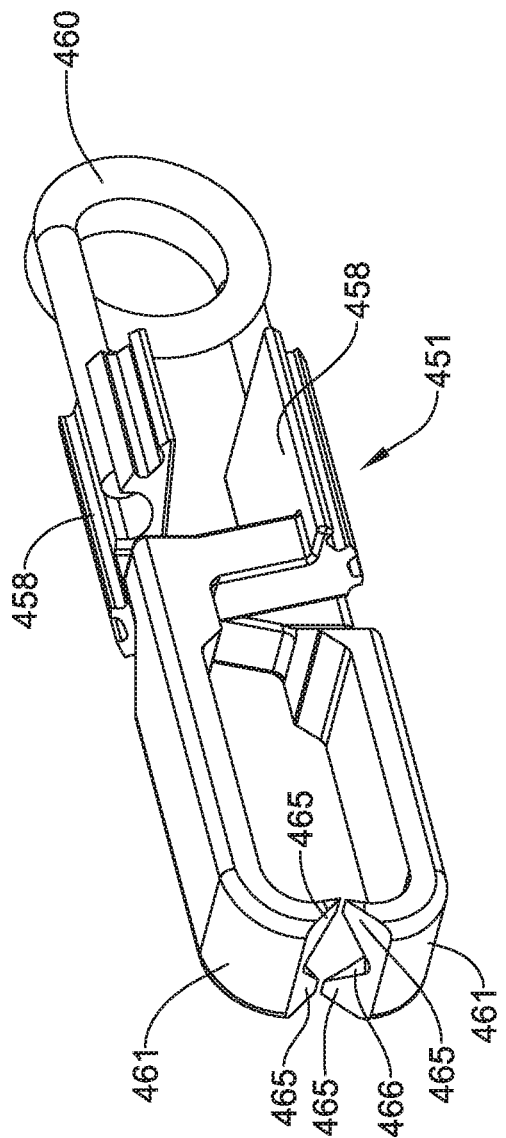

FIGS. 7-9 illustrate different example tissue engagement members. The tissue engagement members illustrated in FIGS. 7-9 may differ in size, shape, geometry, etc. without departing from the scope of the examples contemplated herein. For example, the particular shape and geometries of the end effectors (e.g., jaws, teeth, gripping members, etc.) disclosed herein may be different. However, it is contemplated that any of the features disclosed with respect to an example tissue engagement member may be compatible with any other tissue engagement member disclosed herein.

FIG. 7 illustrates another example tissue engagement member 251. The tissue engagement member 251 may be similar in form and function to the tissue engagement member 51 described above. For example, the tissue engagement member 251 may include jaws 261, gripping members 258 and a spring 260. Additionally, FIG. 7 illustrates that each of the jaws 261 may include a single, flat tooth 265, wherein each tooth 265 faces the other. As described above with respect to the tissue engagement member 52a shown in FIG. 4, each tooth 265 may be sloped such that it is angled toward the coiled portion 260. The direction of the slope enhances tissue engagement by discouraging captured tissue from disengaging.

FIG. 8 illustrates another example tissue engagement member 351. The tissue engagement member 351 may be similar in form and function to other tissue engagement members described above. For example, the tissue engagement member 351 may include jaws 361, gripping members 358 and a spring 360. Additionally, FIG. 8 illustrates that the "top" jaw 361 of FIG. 8 may include a first tooth 365 and a second tooth 375, wherein the first tooth 365 is wider than the second tooth 375. Additionally, the first tooth 365 may be spaced away from the second tooth 375 to create a gap 366 between the first tooth 365 and the second tooth 375. Similarly, the "bottom" jaw 361 of FIG. 8 may include a first tooth 365 and a second tooth 375, wherein the first tooth 365 is wider than the second tooth 375. Additionally, the first tooth 365 may be spaced away from the second tooth 375 to create a gap 366 between the first tooth 365 and the second tooth 375. Additionally, it can be appreciated that the teeth may be arranged such that the first tooth 365 of the top row is aligned with the gap 366 of the bottom row, while the first tooth 365 of the bottom row is aligned with the gap 366 of the top row. In other words, teeth of the top row are designed to interdigitate with the teeth of the bottom row.

Furthermore, it can be appreciated that each of the first teeth 365 and each of the second teeth 375 may be sloped such that they are angled toward the coiled portion 360 (as described above with respect to other tissue engagement members). The direction of the slope enhances tissue engagement by discouraging captured tissue from disengaging.

FIG. 9 illustrates another example tissue engagement member 451. The tissue engagement member 451 may be similar in form and function to other tissue engagement members described above. For example, the tissue engagement member 451 may include jaws 461, gripping members 458 and a spring 460. Additionally, FIG. 9 illustrates that the jaw 461 may each include one or more teeth 465. It can be appreciated that the teeth 465 may include a variety of different of shapes which are oriented in a variety of different configurations. Each jaw 461 illustrated in FIG. 9 may include two teeth 465, wherein the teeth 465 of one jaw 461 may mirror the teeth 465 of the other jaw 461. In other words, the teeth 465 of the "top" jaw may be aligned with the teeth 465 of the "bottom" jaw. Further, FIG. 9 illustrates that the particular arrangement of the teeth 465 results in an aperture 466 located in a central region of the teeth 465.

Furthermore, as described above with respect to other tissue engagement members, each tooth 465 may be sloped such that it is angled toward the coiled portion 460. The direction of the slope enhances tissue engagement by discouraging captured tissue from disengaging.

FIGS. 10-14 illustrate a series of steps to deploy and utilize the tissue retraction system 10 described above. The tissue retraction device 22 may be utilized to lift and reposition target tissue which has been dissected by a clinician. As will be made clear by the following illustrations, as the clinician cuts away target tissue, the tissue retraction device may lift and reposition it, thereby providing the clinician with an unobstructed view of the ongoing procedure.

Figure 10:
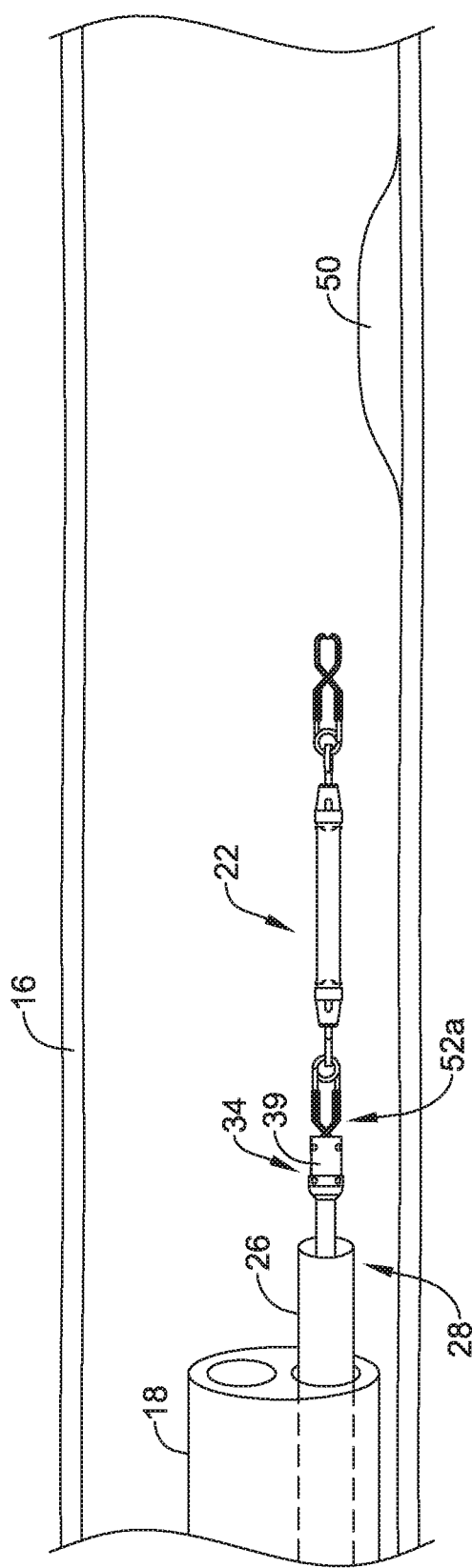
FIGS. 10-14 illustrate a methodology for deploying and attaching an example tissue retraction device.

FIG. 10 illustrates a first step in utilizing the tissue retraction system 10 in a dissection procedure. As described above and illustrated in FIG. 10, the clinician may first advance the manipulator 34 in a proximal-to-distal direction (relative to the distal end 28 of the delivery catheter 26). This forward movement of the manipulator will force the grasping member 39 of the manipulator to push the tissue retraction device 22 forward and out the distal end 28 of the delivery catheter 26. FIG. 10 illustrates the tissue retraction device 22 having been advanced out of the distal end 28 of the delivery catheter 26, whereby it is positioned adjacent to the tissue target 50 (e.g., a cancerous lesion).

Figure 11:
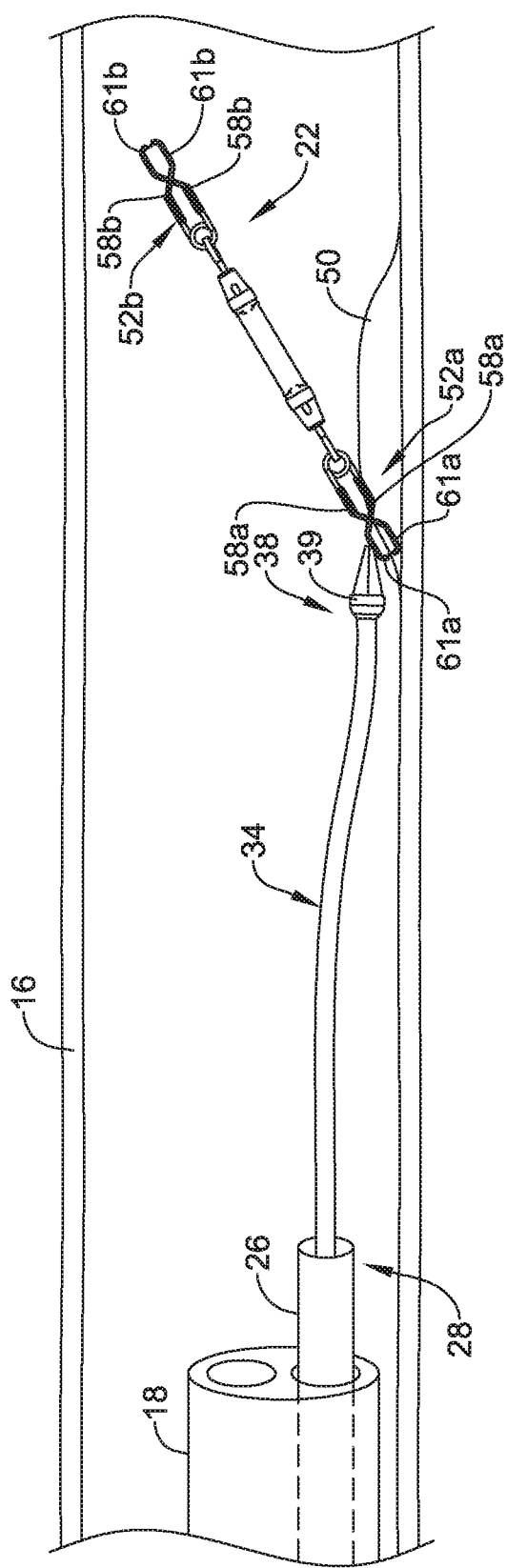

FIG. 11 illustrates an example second step in utilizing the tissue retraction system 10 in a dissection procedure. FIG. 11 illustrates that a clinician may manipulate the distal end 38 of the manipulator 34 to grasp the first engagement member 52a (for clarity, the grasping member 39 is shown in a closed configuration in FIG. 11. It can be appreciated that the grasping member 39 may open up to grasp the first engagement member 52a). For example, the clinician may manipulate the handle 44 of the tissue retraction system 10 to open the jaws of the grasping member 39. Once opened, the jaws of the grasping member may engage the gripping members 58a of the first engagement member 52a. After engaging the gripping members 58a, the clinician may close the jaws of the grasping member 39, thereby opening the jaws 61a of the first engagement member 52a. Using the grasping member 39, the clinician may then position the jaws 61a onto the surface of the target tissue 50. By releasing the grasper 39 from the gripping members 58b, the jaws 61a of the first engagement member 52a may close and attach the jaws 61a (and, by extension, the first engagement member 52a) to the surface of target tissue 50.

Figure 12:
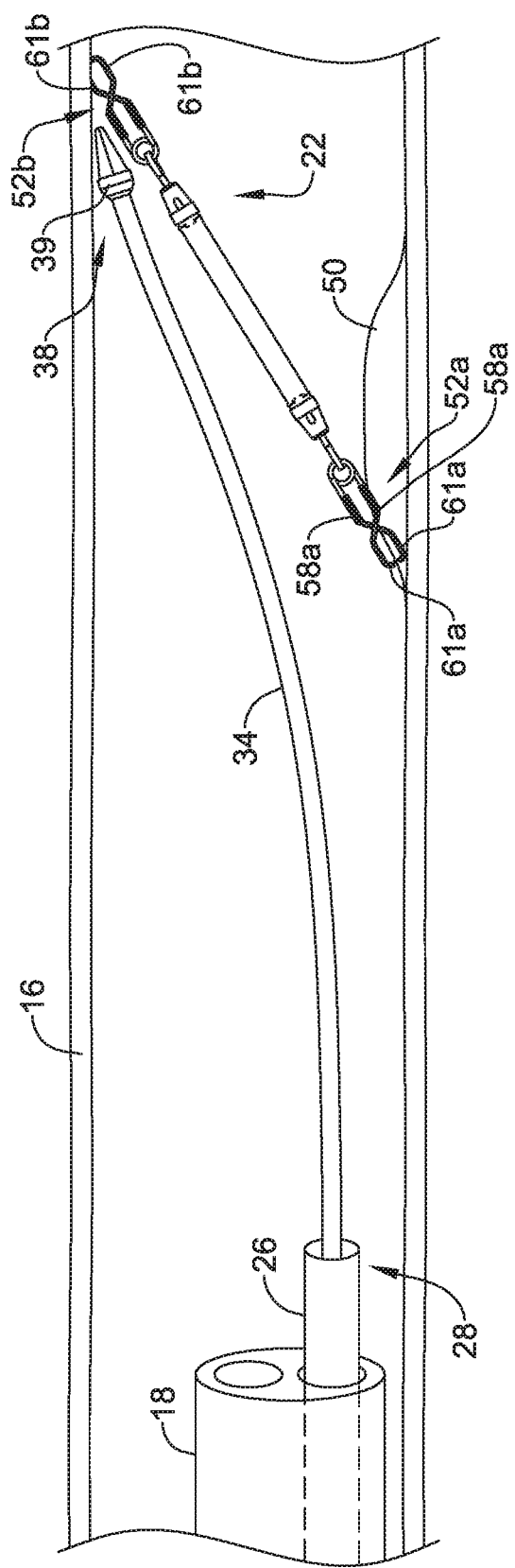

FIG. 12 illustrates an example third step in utilizing the tissue retraction system 10 in a dissection procedure. FIG. 12 illustrates that a clinician may manipulate the distal end 38 of the manipulator 34 to grasp the second engagement member 52b (for clarity, the grasper 39 is shown in a closed configuration in FIG. 12). It can be appreciated that the grasper 39 may open up to grasp the second engagement member 52b. For example, the clinician may manipulate the handle 44 (described above) of the tissue retraction system 10 to open the jaws of the grasper 39. Once opened, the jaws of the grasper may engage the gripping members 58b of the second engagement member 52b. After engaging the gripping members 58b, the clinician may close the jaws of the grasper 39, thereby opening the jaws 61b of the second engagement member 52b. The clinician may then pull on the second engagement member 52b, thereby lengthening the tissue retraction device 22 (as described above with respect to FIG. 2A and FIG. 3). Once the tissue retraction device is elongated to a desired length (which may be confirmed visually via reference markers 66 as described above), the clinician may position the jaws 61b of the second engagement member 52b onto the surface of the target tissue site 50. By releasing the grasping member 39 from the gripping members 58b, the jaws 61b of the second engagement member 52b may close, thereby attaching the jaws 61b (and, by extension, the second engagement member 52b) to the inner surface of body lumen 16.

Figure 13:
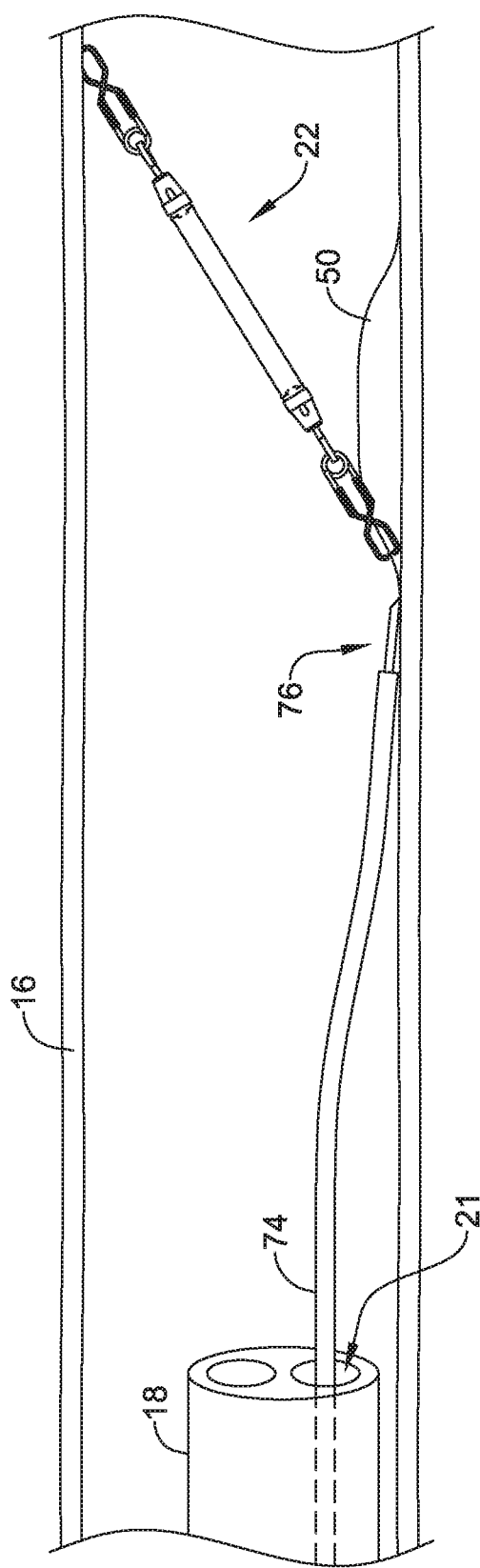

FIG. 13 illustrates an example fourth step in utilizing the tissue retraction system 10 in a dissection procedure. FIG. 13 illustrates that after the tissue retraction device 22 has been attached to both the target tissue site 50 and to the inner surface of the body lumen 16 at a position spaced away from the target tissue site (which places the tissue retraction device 22 in tension), the clinician may exchange the manipulator 34 for a cutting tool 74. The cutting tool 74 may include a cutting member 76 positioned at the target tissue 50. Further, the cutting tool 74 may be advanced within the working channel 21 of the medical device 18 as described above.

Figure 14:
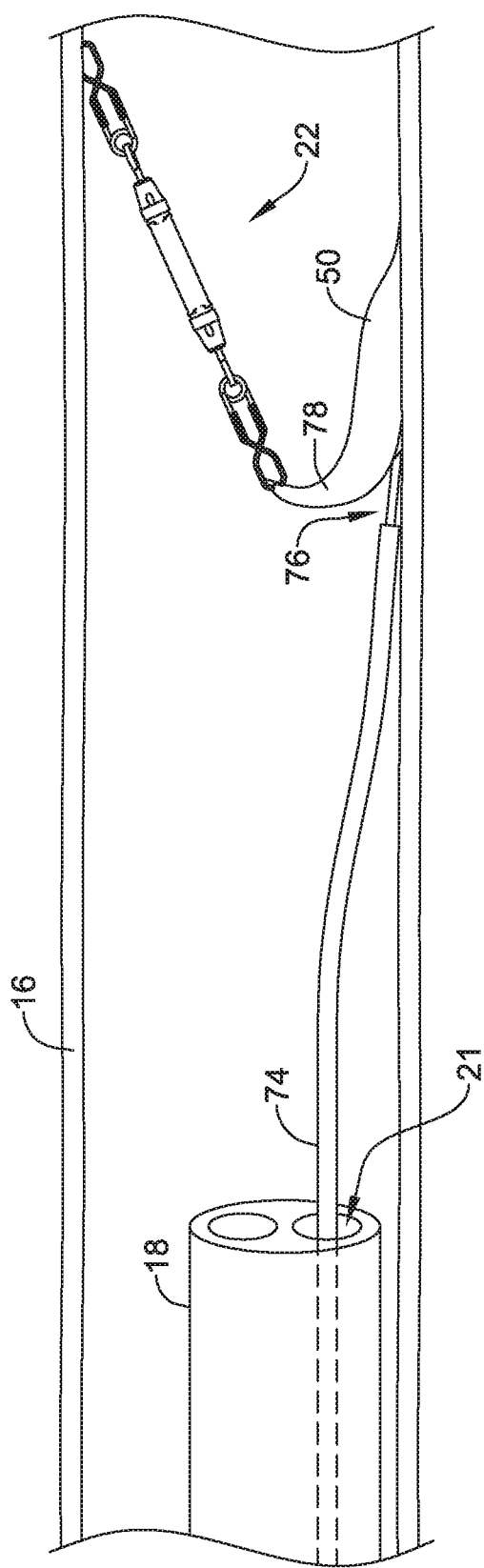

FIG. 14 illustrates an example fifth step in utilizing the tissue retraction system 10 in a dissection procedure. FIG. 14 illustrates the clinician performing the tissue dissection by utilizing the cutting tool 74 to cut a portion of the target tissue 50. As can be appreciated from FIG. 14, as the cutting tool 74 cuts a portion of the target tissue 50, the tissue retraction device 22 retracts (via the retraction of tether members 62a/62b), and thereby lifts the dissected portion 78 of the target tissue 50 up and away from the plane of tissue being cut by the physician. By lifting and retracting the dissected portion 78 of the target tissue 50, a clear, unobstructed view of the procedure is maintained for the clinician. It is noted that, if necessary, the engagement members 52a/52b of the tissue retraction system 10 may be repositioned. In other words, adjustments in tension and/or direction may be imparted into the tissue retraction system 10 as desired.

It should be noted that the features of any of the tissue retraction systems described with respect to particular figures and/or embodiments are not limited to that particular example. Rather, it is contemplated that all of the features or examples disclosed with respect to a single example may be incorporated into any other example disclosed herein.

The materials that can be used for the various components of tissue retraction system 10 and the various devices disclosed herein may include those commonly associated with medical devices. For simplicity purposes, to the extent the following discussion makes reference to tissue retraction system 10, it is not intended to limit the devices and methods described herein only to tissue retraction system 10, as the discussion may be applied to other similar devices disclosed herein.

Tissue retraction system 10 and/or other components of tissue retraction system 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether)phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), styrene ethylene buthylene styrene (SEBS), Thermoplastic Elastomers (TPE) (such as Medalist® available from Teknor Apex and/or Mediprene® available from Hexpol TPE), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of tissue retraction system 10 and/or other components of tissue retraction system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of tissue retraction system 10 and/or other components of tissue retraction system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of tissue retraction system 10 and/or other components of tissue retraction system 10 to achieve the same result.

In some embodiments, a degree of Magnetic Resonance Imaging (Mill) compatibility is imparted into tissue retraction system 10 and/or other components of tissue retraction system 10. For example, tissue retraction system 10 and/or other components of tissue retraction system 10, or portions thereof, may be made of a material that does not substantially distort the image and create substantial artifacts (e.g., gaps in the image). Certain ferromagnetic materials, for example, may not be suitable because they may create artifacts in an MRI image. Tissue retraction system 10 and/or other components of tissue retraction system 10, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A tissue retraction device, comprising:
   a first tissue engagement member including movable jaws, the first tissue engagement member coupled to an elastic member by a coupling assembly, the coupling assembly including:
   a first coupler body having a first end region; and
   a first compression member;
   wherein:
   the first end region of the first coupler body is configured to extend into a portion of a lumen of the elastic member; and
   the compression member is designed to compress the elastic member onto the first coupler body such that the elastic member is fixedly engaged with the coupler body.

2. The tissue retraction device of claim 1, wherein the first end region of the first coupler body includes a channel extending around the circumference thereof.

3. The tissue retraction device of claim 2, wherein the first compression member is designed to compress the elastic member into at least a portion of the channel of the first coupler body.

4. The tissue retraction device of claim 1, wherein the compression member includes a compression ring.

5. The tissue retraction device of claim 1, wherein the compression member includes a suture.

6. The tissue retraction device of claim 1, wherein the coupling assembly further comprising a connection member, wherein the connection member is designed to couple the coupler body to the first tissue engagement member.

7. The tissue retraction device of claim 6, wherein the connection member includes a post member and an attachment member, wherein a first end region of the post member is coupled to the attachment member, and wherein the post member is configured to extend through an aperture of the coupler body.

8. The tissue retraction device of claim 7, wherein the post member further includes a second end region opposite the first end region, and wherein the first end region of the post member includes a first diameter, and wherein the second end region of the post member includes a second diameter larger than the first diameter.

9. The tissue retraction device of claim 8, wherein the aperture of the coupler body includes a first inner diameter, and wherein the second diameter of the post member is larger than the first inner diameter of the aperture.

10. The tissue retraction device of claim 7, wherein the first tissue engagement member includes a first tissue engagement portion and a first spring, and wherein the attachment member is designed to engage the first spring.

11. The tissue retraction device of claim 7, wherein the attachment member is substantially C-shaped.

12. The tissue retraction device of claim 7, wherein the attachment member includes a first fitting and a second fitting, and wherein the first fitting and the second fitting are designed to mate with one another.

13. The tissue retraction device of claim 12, wherein the first fitting and the second fitting are designed to couple the first spring with the first end region of the post member.

14. The tissue retraction device of claim 2, wherein the compression member mates within the channel to sandwich the elastic member between the compression member and the coupler body.

15. A tissue retraction device, comprising:
a first tissue clip rotatably coupled to an elastic member by a first coupling assembly, the first coupling assembly including:
a coupler body having a first end region; and
a compression member;
wherein:
the first end region of the coupler body is configured to be attached to the elastic member.

16. The tissue retraction device of claim 15, further comprising a tubular support member including a lumen extending therein, and wherein at least a portion of the elastic member extends within the lumen of the support member.

17. The tissue retraction device of claim 16, wherein the support member is positioned between the first tissue engagement member and a second tissue engagement member.

18. The tissue retraction device of claim 15, wherein the first end region of the coupler body includes a channel extending around the circumference thereof.

19. The tissue retraction device of claim 18, wherein the first end region of the coupler body is configured to extend into a lumen of the elastic member, and the compression member is designed to compress the elastic member within at least a portion of the channel of the coupler body.

20. A method of dissecting tissue, the method comprising:
advancing a tissue retraction device to a target site, the tissue retraction device including:
a first tissue engagement member coupled to an elastic member by a coupling assembly, the coupling assembly including:
a first coupler body having a first end region; and
a first compression member;
wherein the first end region of the first coupler body is configured to extend into a portion of a lumen of the elastic member;
wherein the compression member is designed to compress the elastic member onto the first coupler body such that the elastic member is fixedly engaged with the coupler body;
manipulating the first tissue engagement member between a first configuration and a second open configuration; and
attaching the first tissue engagement member to the target site.

* * * * *